United States Patent
Endres et al.

(10) Patent No.: US 9,205,405 B2
(45) Date of Patent: Dec. 8, 2015

(54) REDUCED FURFURAL CONTENT IN POLYACRYLIC ACID CROSSLINKED CELLULOSE FIBERS USED IN ABSORBENT ARTICLES

(71) Applicant: The Procter & Gamble Company, Cincinnati, OH (US)

(72) Inventors: Jorg Endres, Frankfurt am Main (DE); Holger Beruda, Schwalbach (DE); Ludwig Busam, Huenstetten (DE); Angel Stoyanov, Federal Way, WA (US)

(73) Assignee: The Procter & Gamble Company, Cincinnati, OH (US)

( * ) Notice: Subject to any disclaimer, the term of this patent is extended or adjusted under 35 U.S.C. 154(b) by 92 days.

(21) Appl. No.: 14/270,598

(22) Filed: May 6, 2014

(65) Prior Publication Data

US 2015/0321171 A1    Nov. 12, 2015

(51) Int. Cl.
*B01J 20/26* (2006.01)

(52) U.S. Cl.
CPC ..................... *B01J 20/267* (2013.01)

(58) Field of Classification Search
CPC ........................................................ B01J 20/26
USPC ......................................................... 502/402
See application file for complete search history.

(56) References Cited

U.S. PATENT DOCUMENTS

| | | | |
|---|---|---|---|
| 4,637,859 A | 1/1987 | Trokhan | |
| 5,137,537 A | 8/1992 | Herron et al. | |
| 5,183,707 A | 2/1993 | Herron et al. | |
| 5,190,563 A | 3/1993 | Herron et al. | |
| 5,447,977 A | 9/1995 | Hansen et al. | |
| 5,549,791 A | 8/1996 | Herron et al. | |
| 5,562,740 A | 10/1996 | Cook et al. | |
| 5,700,254 A | 12/1997 | McDowall et al. | |
| 5,998,511 A | 12/1999 | Westland et al. | |
| 6,306,251 B1 | 10/2001 | Jewell et al. | |
| 6,620,865 B2 | 9/2003 | Westland et al. | |
| 7,513,973 B2 | 4/2009 | Stephens et al. | |
| 7,786,341 B2 | 8/2010 | Schneider et al. | |
| 2003/0105190 A1 | 6/2003 | Diehl et al. | |
| 2007/0270070 A1 | 11/2007 | Hamed | |
| 2008/0119626 A1 | 5/2008 | Fujimaru et al. | |
| 2008/0161512 A1 | 7/2008 | Kawano et al. | |
| 2013/0209749 A1 | 8/2013 | Myangiro et al. | |

FOREIGN PATENT DOCUMENTS

| | | |
|---|---|---|
| EP | 0149880 | 7/1985 |
| WO | WO 95/10996 A1 | 4/1995 |
| WO | WO 00/59430 A1 | 10/2000 |
| WO | WO 02/067809 A2 | 9/2002 |

OTHER PUBLICATIONS

International Search Report and Written Opinion, PCT/US2015/029158, date of mailing Jul. 17, 2015.

*Primary Examiner* — Edward Johnson
(74) *Attorney, Agent, or Firm* — Christian M. Best (57) ABSTRACT

Absorbent articles comprising bleached polycrylic acid crosslinked cellulose fibers with reduced furfural content are disclosed. The reduced furfural content is accompanied by a strong reduction of malodor associated with crosslinked fibers. Methods of furfural reduction include treatment with hydrogen peroxide in the absence of alkaline or other bleaching agents subsequent to curing polyacrylic acid crosslinked cellulose fibers. Some embodiments of treated polyacrylic acid crosslinked cellulose fibers have a furfural content lower than 1.3 ppm. In some embodiments, the reduction of furfural content of the treated crosslinked fibers compared to untreated crosslinked fibers is at least 55%. In some embodiments, furfural content decreases with aging of the treated crosslinked fibers.

20 Claims, 2 Drawing Sheets

REDUCED FURFURAL CONTENT IN POLYACRYLIC ACID CROSSLINKED CELLULOSE FIBERS USED IN ABSORBENT ARTICLES

TECHNICAL FIELD

This disclosure relates to absorbent articles comprising polyacrylic acid crosslinked cellulose fibers, and in particular to reduction of furfural, and accompanying malodor, that is generated during the curing stage of the crosslinking process when making the crosslinked cellulose fibers.

BACKGROUND

Cellulosic fibers are a basic component of absorbent articles such as diapers. These fibers form a liquid absorbent structure, a key element of the absorbent article. Cellulosic fluff pulp, a form of cellulosic fibers, is a suitable fiber for this application because a high void volume, or high bulk, liquid absorbent fiber structure is provided. This structure, however, tends to collapse during wetting, and this reduction in fiber structure bulk reduces the volume of liquid that can be retained in the wetted structure, and also inhibits the wicking of liquid into the unwetted portion of the cellulose fiber structure. Consequently, the potential capacity of the dry high bulk fiber structure is not realized and it is the fiber structure's wet bulk that determines the liquid holding capacity of the overall fiber structure.

Fiber structures formed from crosslinked cellulosic fibers generally have enhanced wet bulk compared to those formed from uncrosslinked fibers. The enhanced bulk is a consequence of the stiffness, twist, and curl imparted to the fibers as a result of crosslinking. Accordingly, crosslinked fibers are advantageously incorporated into absorbent articles to enhance their wet bulk.

Polycarboxylic acids have been used to crosslink cellulose fibers. For example, absorbent structures containing individualized cellulosic fibers crosslinked with a C2-C9 polycarboxylic acid are described in U.S. Pat. No. 5,137,537, U.S. Pat. No. 5,183,707, and U.S. Pat. No. 5,190,563, among others. Absorbent structures made from these individualized, crosslinked fibers exhibit increased dry and wet resilience, and improved responsiveness to wetting, relative to structures containing uncrosslinked fibers. Furthermore, citric acid, a monomeric polycarboxylic acid, is available in large quantities at relatively low prices making it commercially competitive with formaldehyde and formaldehyde-addition products, or urea-glyoxal condensation products.

However, cellulosic fibers crosslinked with monomeric polycarboxylic acids such as citric acid tend to lose their crosslinks over time and revert to an uncrosslinked state. For example, citric acid crosslinked fibers show a considerable loss of crosslinks on storage. Such a reversion of crosslinking generally defeats the purpose of fiber crosslinking, which is to increase the fiber's bulk and capacity. Thus, the useful shelf-life of fibers crosslinked with these monomeric polycarboxylic acids is relatively short and renders the fibers somewhat limited in their utility.

In contrast, polymeric polycarboxylic acid crosslinked fibers, such as those disclosed, for example, in U.S. Pat. No. 6,620,865, exhibit a density that remains substantially unchanged over the lifetime of fibrous webs prepared from these fibers. This resistance to aging or reversion of density relates to the stable intrafiber crosslinks formed using such polymeric crosslinking agents. Cellulose fibers crosslinked with citric acid show a considerable increase in density, accompanied by a loss of bulk and absorbent capacity over time. Generally, the increase in density indicates a decrease in the level of crosslinking (i.e. reversion) in the fibers. In addition to density increase, the loss of crosslinking in the fibrous web results in a less bulky web and, consequently, diminished absorbent capacity and liquid acquisition capability.

Some crosslinking agents can cause discoloration, i.e. yellowing, of the white cellulosic fibers at the elevated temperatures required to effect the crosslinking reaction. A possible mechanism, at least for citric acid, is a dehydration reaction resulting in aconitic acid and a yellow coloration attributable to the C=C chromophore.

Widespread consumer demand for brighter, whiter pulp drives manufacturers to pursue methods for reducing discoloration. Bleaching, for example, is a common method for increasing pulp brightness (as defined by the Technical Association of the Pulp & Paper Industry ("TAPPI") or the International Organization for Standardization ("ISO")). Industrial practice for improving appearance of fluff pulp is to bleach the pulp to increase its brightness. Traditional bleaching agents include elemental chlorine, chlorine dioxide, and hypochlorites. However, bleaching, especially with chlorine-containing agents, can be environmentally harsh, expensive, and a source of manufacturing bottleneck. Accordingly, there have been many attempts to reduce the number, nature, and quantity of bleaching agents used in bleaching methods.

Also, while highly bleached pulps are "whiter" than less-bleached material, such pulps are often still yellow-white in color. Consumer studies indicate a clear preference for blue-white over yellow-white colors, as the former is perceived to be whiter, i.e. fresh, new, and clean, in comparison to the latter, which is considered to be old, faded, or dirty.

Addressing this preference, U.S. Pat. No. 7,513,973, for example, suggests that whiteness attribute, rather than TAPPI or ISO brightness, better correlates with consumer preference for product whiteness, and discloses bleaching methods that seek to improve the Whiteness Index of cellulosic fibers crosslinked with polymeric polycarboxylic crosslinking agents, such as methods that involve the use of sodium hydroxide and/or hydrogen peroxide.

It is generally accepted that the active mechanism in chromophore elimination in bleaching operations that include hydrogen peroxide involves the perhydroxyl ion $OOH^-$. The formation of the perhydroxyl anion can be enhanced, for example, by increasing the pH during the bleaching stage, according to the following reaction:

$$H_2O_2 + OH^- \leftrightarrows OOH^- + H_2O$$

Accordingly, industry practice is to perform hydrogen peroxide bleaching in alkaline systems, such as by adding an alkaline agent (such as sodium hydroxide) in coordination with hydrogen peroxide in the bleaching stage.

In U.S. Pat. No. 5,562,740, the combination of an alkaline agent (such as sodium hydroxide) with an oxidizing agent (such as hydrogen peroxide) has been observed, in a bleaching stage at a pH of at least 5.5, to reduce the "smoky and burnt" odor of cellulosic fibers crosslinked with alpha-hydroxy carboxylic acid crosslinking agents such as citric acid, in addition to improving brightness. The '740 patent theorizes that the malodor is due to the collective presence of a host of substances including volatile phenolics, hydrogen sulfide, various sugar decomposition products (such as furfural, methyl furfural, and guaicols), and citric acid anhydrides, and that the odor reduction may be due to the possible reduction of such substances by the combination of alkaline and oxidizing agents at a pH of at least 5.5.

Although this "burnt" odor originally became identified as a characteristic of citric acid crosslinked cellulosic fibers specifically, such as in the '740 patent, it has become known that the "burnt" odor also accompanies cellulosic fibers crosslinked with polymeric polycarboxylic acids, such as polyacrylic acid, as well.

Accordingly there remains a need for absorbent articles comprising cellulose fibers crosslinked with polymeric polycarboxylic acids, which cellulose fibers exhibit high bulk, increased brightness and whiteness, and reduced malodor.

SUMMARY

Bleached polyacrylic acid crosslinked cellulose fibers with reduced furfural content have been identified, as well as methods for reducing the furfural content of polyacrylic acid crosslinked cellulose fibers, by treatment of the crosslinked fibers with hydrogen peroxide, are disclosed herein for use in absorbent articles.

Unexpectedly, it was found that a reduction in furfural levels was accompanied by a strong reduction of the "burnt" malodor associated with polyacrylic acid crosslinked cellulose fibers. The invention relates to absorbent articles comprising polyacrylic acid crosslinked cellulosic fibers, the polyacrylic acid crosslinked cellulosic fibers being subsequently treated with hydrogen peroxide, in an amount of from 0.045 kg to 9.07 kg (0.1 to 20 pounds) per ADMT of fiber, in the absence of sodium hydroxide. The amount of hydrogen peroxide may be at least from 1.59 kg to 9.07 kg (3.5 to 20 pounds) per ADMT of fiber, or may be from 2.27 kg to 9.07 kg (5 pounds to 20 pounds) per ADMT of fiber. The amount of furfural in the treated crosslinked fibers reduces from a first value determined at least one day after treatment of the crosslinked fibers to a second, subsequent value determined up to 21 days after treatment. The polyacrylic acid crosslinked cellulosic fibers have been treated with hydrogen peroxide prior to having been incorporated into the absorbent article. The polyacrylic acid crosslinked cellulosic fibers may have less than 1.3 ppm, or less than 0.8 ppm, or less than 0.4 ppm furfural up to 21 days after treatment. The reduction of furfural from the first value to the second value may be at least 25%, or at least 35%, or at least 45%, or at least 48%. The subsequent treatment of the polyacrylic acid crosslinked cellulosic fibers may be in the absence of alkaline or other bleaching agents.

The invention further relates to absorbent articles comprising polyacrylic acid crosslinked cellulosic fibers, wherein the polyacrylic acid crosslinked cellulosic fibers have less than 1.3 ppm furfural, for example by having been subsequently treated with hydrogen peroxide in the absence of alkaline or other bleaching agents prior to having been incorporated into the absorbent article. The polyacrylic acid crosslinked cellulosic fibers may have less than 0.8 ppm furfural, or may have less than 0.4 ppm furfural.

The invention also refers to absorbent articles comprising polyacrylic acid crosslinked cellulosic fibers, wherein the polyacrylic acid crosslinked cellulosic fibers are subsequently treated with hydrogen peroxide, in an amount of from 0.045 kg to 9.07 kg (0.1 to 20 pounds) per ADMT of fiber, in the absence of alkaline agents (i.e. in the absence of alkaline of other bleaching agents). The amount of furfural in the treated crosslinked fibers is reduced by at least 55%, or by at least 60%, or by at least 75%, as measured up to 21 days after the treatment, versus the untreated fibers (i.e. versus the same polyacrylic acid crosslinked cellulosic fibers except not given the aforementioned subsequent treatment). The polyacrylic acid crosslinked cellulosic fibers have been treated with hydrogen peroxide prior to having been incorporated into the absorbent article The invention also refers to a method of making an absorbent article, the absorbent article comprising polyacrylic acid crosslinked cellulosic fiber. The method comprises the reduction of the furfural content of polyacrylic acid crosslinked cellulosic fibers prior to introducing the polyacrylic acid crosslinked cellulosic fibers into the absorbent article. Reducing the furfural content of polyacrylic acid crosslinked cellulosic fibers comprises applying hydrogen peroxide alone, in a bleaching stage subsequent to a curing stage, to polyacrylic acid crosslinked cellulosic fibers in an amount of from 0.045 kg to 9.07 kg (0.1 to 20 pounds) per ADMT of fiber and at a pH of between 4.5 and 5. The amount of hydrogen peroxide may be from 2.27 kg to 9.07 kg (5.0 pounds to 20 pounds), or from 2.27 kg to 4.54 kg (5.0 pounds to 10 pounds), or from 1.36 kg to 4.54 kg (3.0 pounds to 10 pounds) per ADMT of fibers. The amount of furfural in the treated crosslinked fibers reduces from a first value determined at least one day after the treatment of the crosslinked fibers to a second, subsequent value determined up to 21 days after treatment.

Moreover, the invention relates to a method of reducing the malodor associated with the presence of furfural in polyacrylic acid crosslinked cellulosic fibers comprising applying hydrogen peroxide in the absence of alkaline agents to the crosslinked cellulosic fibers subsequent to curing the crosslinked cellulosic fibers and thereby reduce the furfural content of the crosslinked cellulosic fibers by at least 55% versus the untreated fibers, (i.e. the same polyacrylic acid crosslinked cellulosic fibers except not given the aforementioned subsequent treatment). The treated crosslinked cellulosic fibers are subsequently incorporated into an absorbent article.

The concepts, features, methods, and component configurations briefly described above are clarified with reference to the accompanying drawings and detailed description below.

DETAILED DESCRIPTION

Polyacrylic Acid Crosslinked Cellulosic Fibers

As noted above, although a "burnt" odor has been identified as a characteristic of citric acid crosslinked cellulosic fibers specifically, it has become known that the malodor also accompanies cellulosic fibers crosslinked with polymeric polycarboxylic acids, such as polyacrylic acid, as well.

It is found that furfural in cellulose fibers crosslinked with polymeric polycarboxylic acids is reduced by treatment of the fibers subsequent to crosslinking with hydrogen peroxide. The extent of furfural reduction can be increased when hydrogen peroxide is used in the absence of sodium hydroxide or other alkaline agents relative to the extent of furfural reduction in the presence of such agents. It is also unexpectedly found that a reduction in furfural levels is accompanied by a strong reduction of the malodor associated with the fibers. Accordingly, it is theorized that furfural is the main odoriferous volatile organic compound causing the malodor, and that treatment with hydrogen peroxide replaces the compound with reaction products that impart a clean, fresh odor. Hemicellulose, which accompanies the cellulose fibers obtained from wood during the pulping process, is considered the main source for furfural generation during thermal treatment (e.g., curing) of the cellulose fibers, according to the following proposed mechanism.

Thus, polyacrylic acid crosslinked cellulosic fibers can be subsequently treated with hydrogen peroxide, wherein the amount of furfural in the treated polyacrylic acid crosslinked fibers reduces from a first value determined at least one day after treatment of the polyacrylic acid crosslinked fibers to a second value determined up to 21 days after treatment.

It is also found that in some cases, the furfural reduction with hydrogen peroxide in the absence of an alkaline agent such as sodium hydroxide is more pronounced when compared to subsequent treatment with hydrogen peroxide in the presence of such an alkaline agent. Thus, contrary to expectation, it was found that pH adjustment of the crosslinked fibers to at least 5.5, such as by use of an alkaline agent such as sodium hydroxide, is not required to effect the reduction of furfural and accompanying malodor, thereby potentially reducing the use of (or need for) such agents in the bleaching process.

The bleached polyacrylic acid crosslinked fibers discussed herein are made from polyacrylic acid crosslinked cellulosic fibers. These crosslinked cellulosic fibers are obtained by treating cellulosic fibers with an amount of a polyacrylic acid crosslinking agent to provide intrafiber crosslinked cellulosic fibers having increased bulk.

Polyacrylic acid crosslinked cellulosic fibers and methods for making polyacrylic acid crosslinked cellulosic fibers are described in U.S. Pat. No. 5,549,791, U.S. Pat. No. 5,998,511, U.S. Pat. No. 6,306,251, for example, and bleached polyacrylic acid crosslinked cellulosic fibers are described in U.S. Pat. No. 7,513,973.

Polyacrylic acid crosslinked cellulosic fibers can be prepared by applying polyacrylic acid to the cellulosic fibers in an amount sufficient to achieve intrafiber crosslinking. The amount applied to the cellulosic fibers can be from 1 to 10 percent by weight based on the total weight of fibers. Crosslinking agent may be applied in and amount from 4 to 6 percent by weight based on the total weight of dry fibers.

Polyacrylic acid crosslinked cellulosic fibers can be prepared using a crosslinking catalyst. Suitable catalysts can include acidic salts, ammonium sulfate, and alkali metal salts of phosphorous-containing acids. In one example, the crosslinking catalyst is sodium hypophosphite. The amount of catalyst used can vary from 0.1 to 5 percent by weight, based on the total weight of dry fibers.

Although available from other sources, cellulosic fibers useful for making the bleached polyacrylic acid crosslinked cellulosic fibers in accordance with the present disclosure are derived primarily from wood pulp. Suitable wood pulp fibers for use with the invention can be obtained from well-known chemical processes such as the kraft and sulfite processes, with or without subsequent bleaching. The pulp fibers may also be processed by thermomechanical, chemithermomechanical methods, or combinations thereof. Usually the pulp fiber is produced by chemical methods, although ground wood fibers, recycled or secondary wood pulp fibers, and bleached or unbleached wood pulp fibers can be used. A suitable starting material is prepared from long-fiber coniferous wood species, such as Southern pine, Douglas fir, spruce, and hemlock. Details of the production of wood pulp fibers are known to those skilled in the art. Suitable fibers are commercially available from a number of companies, including the Weyerhaeuser Company. For example, suitable cellulose fibers produced from southern pine that are usable in making the present invention are available from the Weyerhaeuser Company under the designations CF416, CF405, NB416, NF405, FR416, and FR516.

Wood pulp fibers suitable for use in accordance with the present disclosure can also be pretreated prior to use. This pretreatment may include physical treatment, such as subjecting the fibers to steam, or chemical treatment. Although not to be construed as a limitation, examples of pretreating fibers include the application of fire retardants to the fibers, and surfactants or other liquids, such as solvents, which modify the surface chemistry of the fibers. Other pretreatments include incorporation of antimicrobials, pigments, and densification or softening agents. Fibers pretreated with other chemicals, such as thermoplastic or thermosetting resins may be used as well. Another kind of physical pretreatment is subjecting the fibers to plasma, including corona discharge, to improve the impregnation process of the crosslinking agent. Combinations of pretreatments may also be employed.

Polyacrylic acid crosslinked cellulosic fibers suitable for use in accordance with the present disclosure may be prepared by a system and apparatus as described in U.S. Pat. No. 5,447,977, for example. The following description of the crosslinking process refers to this system as an illustrative example, although any suitable system may be employed.

Briefly, the system includes a conveying device for transporting a mat or web of cellulose fibers through a fiber treatment zone; an applicator for applying a treatment substance from a source to the fibers at the fiber treatment zone; a fiberizer for separating the individual cellulose fibers comprising the mat to form a fiber output comprised of substantially unbroken and essentially singulated cellulose fibers; a dryer coupled to the fiberizer for flash evaporating residual moisture; and a controlled temperature zone for additional heating of fibers and an oven for curing the crosslinking agent, to form dried and cured individualized crosslinked fibers.

As used herein, the term "mat" refers to any nonwoven sheet structure comprising cellulose fibers or other fibers that are not covalently bound together. The fibers include fibers obtained from wood pulp or other sources including cotton rag, hemp, grasses, cane, cornstalks, cornhusks, or other suitable sources of cellulose fibers that may be laid into a sheet. The mat of cellulose fibers is preferably in an extended sheet form, and may be one of a number of baled sheets of discrete size or may be a continuous roll. For the avoidance of doubt, the term "mat" does not refer to the fibrous structure as it is incorporated into the absorbent article or which forms the absorbent article. Instead, the mat undergoes subsequent process steps, as described below, during which the mat is typically disintegrated again.

Each mat of cellulose fibers is transported by a conveying device, for example, a conveyor belt or a series of driven rollers. The conveying device carries the mats through the fiber treatment zone. At the fiber treatment zone, a crosslinking agent solution is applied to the mat of cellulose fibers. The crosslinking agent solution is applied to one or both surfaces of the mat using any one of a variety of methods known in the art, including spraying, rolling, or dipping. Once the crosslinking agent solution has been applied to the mat, the solution may be uniformly distributed through the mat, for example, by passing the mat through a pair of rollers.

After the mat's fibers have been treated with the crosslinking agent, the impregnated mat is fiberized by feeding the mat through a hammermill. The hammermill disintegrates the mat into its component individual cellulose fibers, which are then air conveyed through a drying unit to remove the residual moisture. The fibrous mat may be wet fiberized.

The resulting treated pulp is then air conveyed through an additional heating zone (e.g. a dryer) to bring the temperature of the pulp to the cure temperature. The dryer can include a first drying zone for receiving the fibers and removing residual moisture from the fibers via a flash-drying method, and a second heating zone for curing the crosslinking agent, to allow the chemical reaction (in this case: esterification), to be completed. Alternatively, the treated fibers are blown through a flash-dryer to remove residual moisture, heated to a curing temperature, and then transferred to an oven where the treated fibers are subsequently cured. Overall, the treated fibers are dried and then cured for a sufficient time and at a sufficient temperature to achieve crosslinking Typically, the fibers are oven-dried and cured for 1 to 20 minutes at a temperature from 120° C. to 200° C. The pH of the fibers is generally around 4.5 to 5.

A bleaching stage typically follows the curing stage. This disclosure provides methods for making bleached polyacrylic acid crosslinked cellulosic fibers. In such methods, polyacrylic acid crosslinked cellulosic fibers are subsequently treated—that is, treated after crosslinking reaction is completed and the fibers are cured—with one or more bleaching agents to provide polyacrylic acid crosslinked cellulosic fibers having reduced amounts of furfural, and accompanying reduced malodor.

The bleaching agent is applied to the polyacrylic acid crosslinked cellulosic fibers. The bleaching agent may be hydrogen peroxide. Alternatively, the bleaching agent is a combination of hydrogen peroxide and sodium hydroxide. Other possible bleaching agents include peroxy acids (e.g. peracetic acid), sodium peroxide, chlorine dioxide, sodium chlorite, and sodium hypochlorite. Mixture of bleaching agents may also be used. Due to environmental and health concerns, bleaching agents other than chlorine-containing agents are generally preferred.

The polyacrylic acid crosslinked cellulosic fibers can be treated with from 0.045 kg (0.1 pounds) to 9.07 kg (20 pounds) hydrogen peroxide per air dried metric ton of fiber. An air dry metric ton, also referred to as "ADMT" (1000 kg), is a weight measurement for wood pulp. Per TAPPI standards, an air dry metric ton has a dry solids (fiber) content of 90%. Thus the aforementioned range corresponds to about 0.005 wt % to about 1.01 wt % chemical on pulp ("COP"). The fibers may be treated with from 1.36 kg (3 pounds) to 4.54 kg (10 pounds) hydrogen peroxide per ADMT of fiber (about 0.15 wt % to about 0.5 wt % COP). The fibers may be treated with 2.27 kg (5 pounds) hydrogen peroxide per ADMT of fiber (about 0.35 wt % COP). The amount of hydrogen peroxide may, in some environments, be limited by factors such as safe chemical handling practice, application method(s), application apparatus, and so forth. However, the disclosure is not so limited, and encompasses any level of hydrogen peroxide effective to reduce furfural levels in polyacrylic acid crosslinked cellulose fibers.

In the method, the bleaching agent may be applied to polyacrylic acid crosslinked cellulosic fibers immediately after curing by spraying hydrogen peroxide onto the fibers by any suitable means. In a lab environment, this may be accomplished by spraying moistened polyacrylic acid crosslinked fibers placed into a mylar aluminum sealable bag with an aqueous solution of hydrogen peroxide. In a mill environment, this can be accomplished by spraying an aqueous solution of hydrogen peroxide into an air stream containing polyacrylic acid crosslinked fibers. Any suitable application method may be used.

The hydrogen peroxide may be applied to polyacrylic acid crosslinked cellulosic fibers in the presence of alkaline agents such as sodium hydroxide. For example, up to 5 pounds sodium hydroxide per ADMT of fiber can be applied to the fibers together with the hydrogen peroxide. Alternatively, the hydrogen peroxide may be applied in the absence of sodium hydroxide, and/or in the absence of any alkaline or other bleaching agents. The pH of the hydrogen peroxide solution applied to the fibers may be between 4.5 and 5. As shown below, furfural content was observed, in some experiments, to be reduced to a greater extent after hydrogen peroxide application in the absence of sodium hydroxide, as compared to hydrogen peroxide application in the presence of sodium hydroxide. Hydrogen peroxide can be applied to polyacrylic acid crosslinked cellulosic fibers alone, that is, in the absence of any other chemical compound or reagent besides water.

Furfural content can be determined by any suitable method, such as standard GC-FID methods or otherwise, and the reduction of furfural content can be calculated by comparing the content measured at two (or more) different times after furfural is initially generated. Due to the different reaction rates of initial furfural generation and subsequent furfural reduction, it was found that furfural measurements were best taken at two points between 1 and 21 days after hydrogen peroxide treatment. For example, in a mill environment, it is typical that the cured fibers, after bleaching, are baled while still retaining heat from the curing stage, and thus it is possible that this residual heat may prolong the furfural generation reaction (even after hydrogen peroxide treatment and initiation of the furfural reduction reaction) until the fibers have cooled. Accordingly, initial furfural measurements were taken at least one day after treatment with hydrogen peroxide. The subsequent furfural measurements were taken after allowing the bleached polyacrylic acid crosslinked cellulosic fibers to be aged, to assure sufficient time for the hydrogen peroxide reduction of furfural content to reach equilibrium. In a production setting, the aging may take place as the fibers are processed or handled after treatment. For example, in a mill environment, after bleaching, the crosslinked fibers are typically conveyed to a baling device in which the product fibers are baled and wrapped prior to shipment.

Absorbent Articles

The bleached polyacrylic acid crosslinked cellulosic fibers produced in accordance with the present disclosure are incorporated in absorbent articles. "Absorbent articles" refers to products that absorb and contain body exudates, and, more specifically, refers to products that are placed against or in proximity to the body of the wearer to absorb and contain the various exudates discharged from the body. Absorbent articles include diapers and pants (to be worn by babies, infants and/or adults), absorbent inserts for diapers or pants, feminine care absorbent articles such as sanitary napkins and pantiliner, breast pads and the like. The term "absorbent article" as used herein also refers to disposable products such as care mats, bibs, wipes (dry and wet wipes) for personal hygiene as well as to paper products.

As used herein, the term "body exudates" includes, but is not limited to, urine, blood, vaginal discharges, breast milk, sweat and fecal matter.

The absorbent articles of the present invention are disposable. Disposable absorbent article refers to an article that is disposed or discarded after a limited number of usage events over varying lengths of time, for example, less than 5 events, less than 2 events, or less than 2 events. Typically, the disposable absorbent article is intended to be disposed after single use.

Generally, absorbent articles which are placed against or in proximity to the body of a wearer, such as diapers, pants and feminine hygiene products, may comprise a topsheet, backsheet, an absorbent core and optionally an acquisition-distribution system, which may consist of one or more layers, such as an upper layer towards the topsheet and a lower layer towards the backsheet. The absorbent core is normally placed between the backsheet and the topsheet, the optional acquisition-distribution system is typically placed between the absorbent core and the topsheet. The polyacrylic acid crosslinked cellulosic fibers described herein may be comprised by the absorbent core and/or by the acquisition-distribution system of the absorbent article. For example, one or more layers, such as the lower layer, of the acquisition-distribution system may comprise or may consist of the polyacrylic acid crosslinked cellulosic fibers. Also, for single layer acquisition-distribution system, the single layer may comprise or may consist of the polyacrylic acid crosslinked cellulosic fibers. Where the polyacrylic acid crosslinked cellulosic fibers are comprised by the absorbent core, the absorbent core may further comprise other absorbent material, such as non-cross-linked cellulose fibers (pulp fibers), superabsorbent polymer (e.g. in particulate form) or combinations thereof. The absorbent core may comprise from 10 wt % to 100 wt %, or from 20 wt % to 80 wt % of the polyacrylic acid crosslinked cellulosic fibers disclosed herein.

"Diaper" and "pant" refers to an absorbent article generally worn by infants and incontinent persons about the lower torso so as to encircle the waist and legs of the wearer and that is specifically adapted to receive and contain urinary and fecal waste. In a pant, as used herein, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened). In a diaper, the waist opening and leg openings are only formed when the diaper is applied onto a wearer by (releasable) attaching the longitudinal edges of the first and second waist region to each other on both sides by a suitable fastening system.

A feminine care absorbent article is a personal care product used by women during menstruation to absorb and retain menses, vaginal discharge, and other bodily functions related to vulva. Feminine care absorbent articles include paniliners and sanitary napkins. The term "sanitary napkin" as used herein refers to an absorbent article which is worn by females adjacent to the pudendal region that is intended to absorb and contain the various exudates which are discharged from the body. The term "pantiliner" as used herein refers to an absorbent article that is less bulky than a sanitary napkin and is generally worn by women between their menstrual periods.

A "paper product" refers to a wet-formed fibrous structure comprising cellulose fibers, such as the polyacrylic acid crosslinked cellulosic fibers disclosed herein. Paper products include tissue-towel paper products, such as toilet tissue and paper towels, table napkins, bath tissue and the like. A tissue-towel paper product might for example be a conventional felt-pressed or conventional wet-pressed tissue paper. Examples of paper products are disclosed in US2013/0209749 and U.S. Pat. No. 4,637,859.

Figure 1:
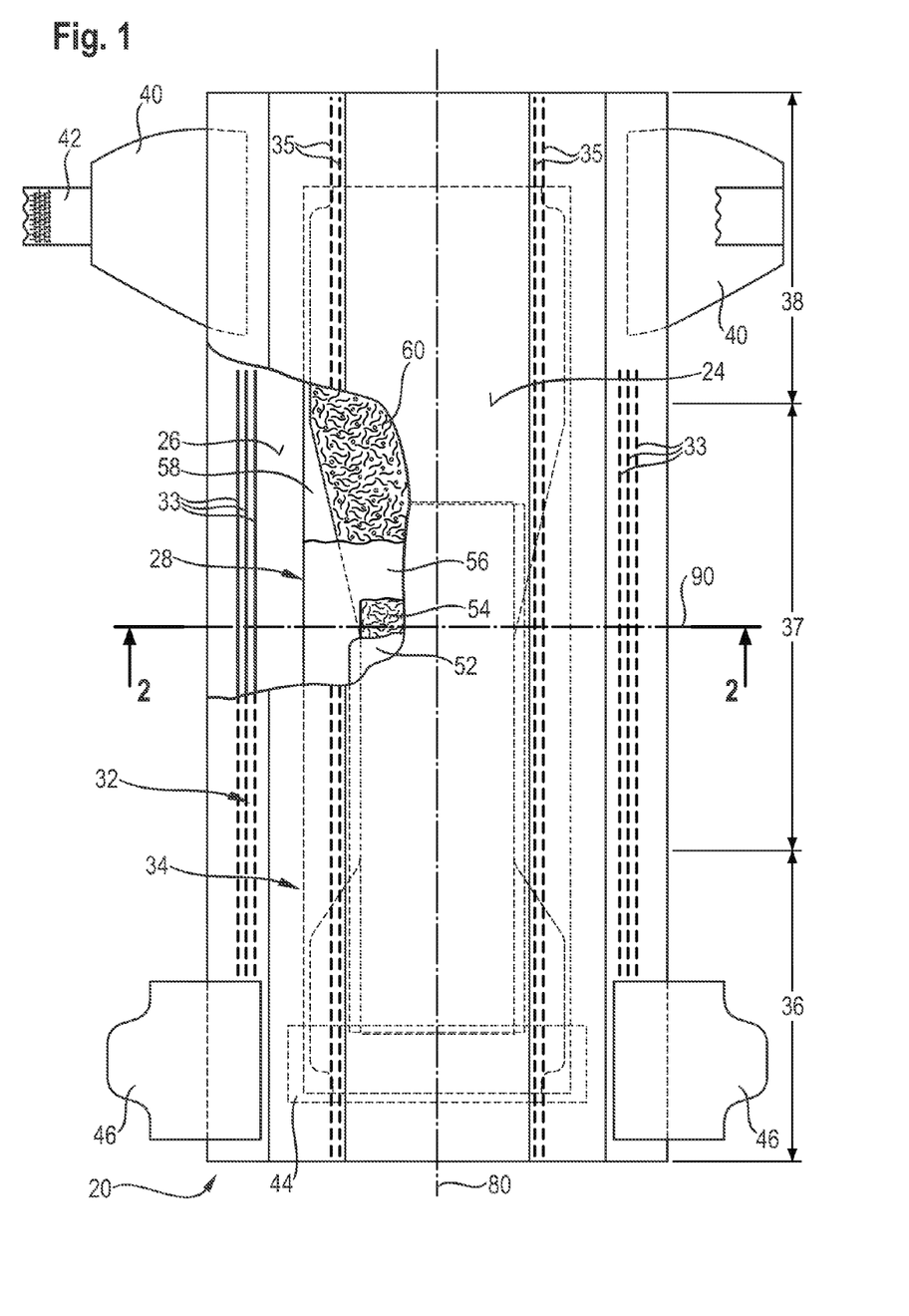
FIG. 1 is a top view of an exemplary absorbent article in the form of a diaper according to the invention with some layers partially removed.
Figure 2:
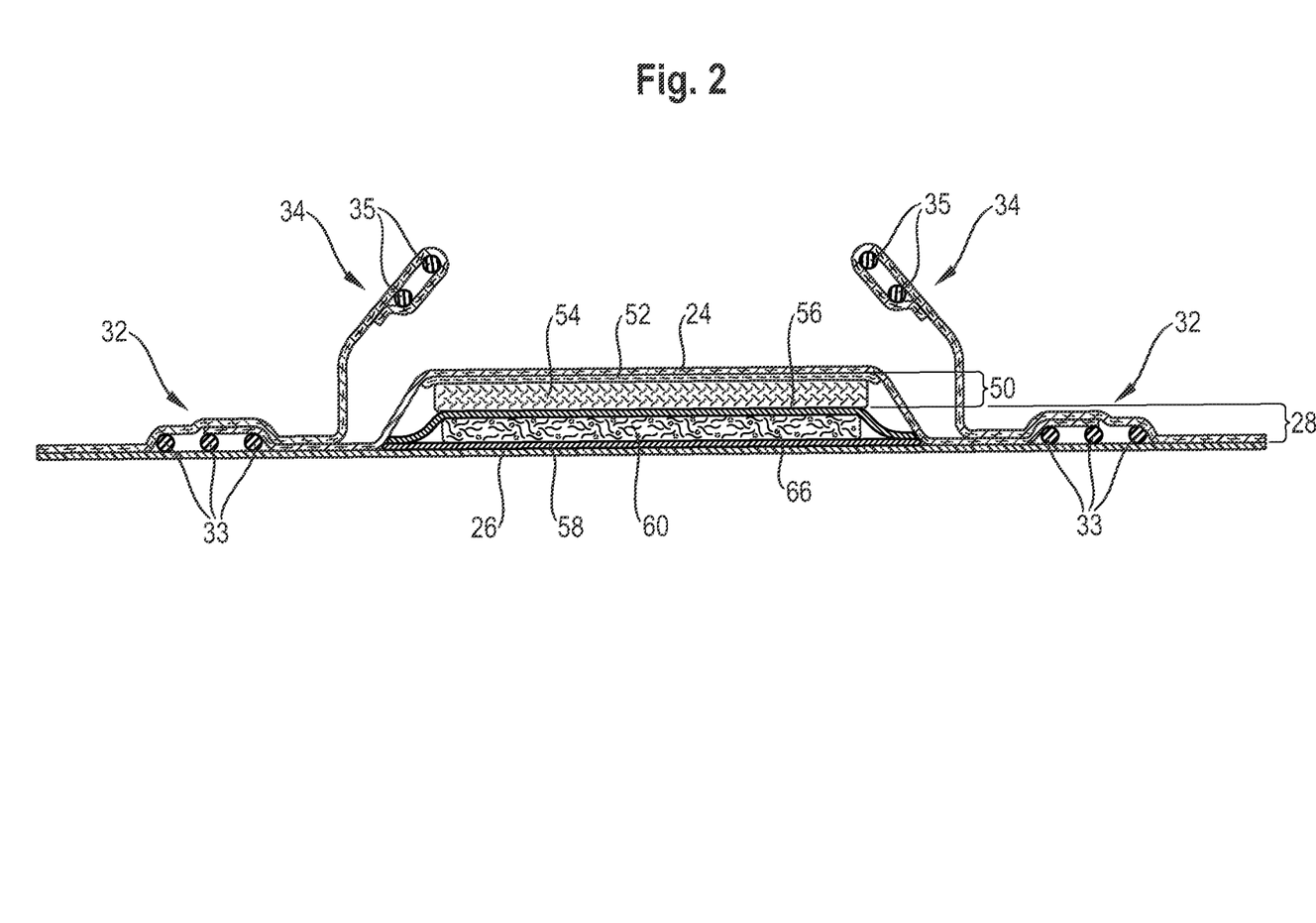
FIG. 2 is a transversal cross-section of the diaper of FIG. 1.

A typical disposable absorbent article of the present invention that is placed against or in proximity to the body of the wearer to absorb and contain the various exudates discharged from the body, is represented in FIGS. 1 and 2 in the form of a diaper 20.

In more details, FIG. 1 is a plan view of an exemplary diaper 20, in a flat-out state, with portions of the diaper being cut-away to more clearly show the construction of the diaper 20. This diaper 20 is shown for illustration purpose only as the structure of the present invention may be comprised in a wide variety of diapers or other absorbent articles.

As shown in FIGS. 1 and 2, the absorbent article, here a diaper, can comprise a liquid pervious topsheet 24, a liquid impervious backsheet 26, an absorbent core 28 which is positioned between f the topsheet 24 and the backsheet 26. The absorbent core 28 can absorb and contain liquid received by the absorbent article and may comprise absorbent materials 60, such as superabsorbent polymer particles 66 and/or cellulose fibers, as well as other absorbent and non-absorbent materials commonly used in absorbent articles (e.g. thermoplastic adhesives immobilizing the superabsorbent polymer particles). The absorbent material and non-absorbent material may be wrapped within a substrate (e.g. one or more nonwovens, tissues etc.) such as by an upper core cover layer 56 facing towards the topsheet and a lower cover layer 58 facing towards the backsheet. Such upper and lower core cover layers may be made of nonwovens, tissues or the like and may be attached to each other continuously or discontinuously, e.g. along their perimeter The absorbent articles of the invention, especially diapers and pants, may comprise an acquisition layer 52, a distribution layer 54, or combination of both (all herein collectively referred to as acquisition-distribution system "ADS" 50). The function of the ADS 50 is typically to quickly acquire the fluid and distribute it to the absorbent core in an efficient manner. The ADS may comprise one, two or more layers. In the examples below, the ADS 50 comprises two layers: a distribution layer 54 and an acquisition layer 52 disposed between the absorbent core and the topsheet.

The ADS may be free of superabsorbent polymer. The prior art discloses many types of acquisition-distribution systems, see for example WO2000/59430, WO95/10996, U.S. Pat. No. 5,700,254, WO02/067809.

The function of a distribution layer 54 is to spread the insulting fluid liquid over a larger surface within the article so that the absorbent capacity of the absorbent core can be more efficiently used. Distribution layers may be made of a non-woven material based on synthetic or cellulosic fibers and having a relatively low density. The distribution layer may typically have an average basis weight of from 30 to 400 g/m$^2$, in particular from 80 to 300 g/m$^2$.

The distribution layer may for example comprise at least 50%, or 60%, or 70%, or 80%, or 90% by weight of cross-linked cellulose fibers, such as the polyacrylic acid crosslinked cellulosic fibers disclosed herein. The distribution layer may also consist completely of the polyacrylic acid crosslinked cellulosic fibers disclosed herein. The cross-linked cellulosic fibers may be crimped, twisted, or curled, or a combination thereof including crimped, twisted, and curled. The cross-linked cellulosic fibers provide higher resilience and therefore higher resistance to the first absorbent layer against the compression in the product packaging or in use conditions, e.g. under baby weight. This provides the core with a relatively high void volume, permeability and liquid absorption, and hence reduced leakage and improved dryness.

The distribution layer comprising cross-linked cellulose fibers, such as the polyacrylic acid crosslinked cellulosic fibers disclosed herein, may comprise other fibers, but this layer may advantageously comprise at least 50%, or 60%, or 70%, or 80%, or 90% or even up to 100%, by weight of the layer, of cross-linked cellulose fibers such as the polyacrylic acid crosslinked cellulosic fibers disclosed herein. Examples of such mixed layer of cross-linked cellulose fibers may comprise 70% by weight of chemically cross-linked cellulose fibers, 10% by weight polyester (PET) fibers, and 20% by weight untreated pulp fibers. In another example, the layer of cross-linked cellulose fibers may comprise 70% by weight chemically cross-linked cellulose fibers, 20% by weight lyocell fibers, and 10% by weight PET fibers. In another example, the layer may comprise 68% by weight chemically cross-linked cellulose fibers, 16% by weight untreated pulp fibers, and 16% by weight PET fibers.

The absorbent article 20 may further comprise an acquisition layer 52, whose function is to quickly acquire the fluid away from the topsheet so as to provide a good dryness for the wearer. The acquisition layer 52 is typically placed directly under the topsheet and below the distribution layer. The acquisition layer may typically be or comprise a non-woven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (such as a 50/50 or 40/60 mix of 6 denier and 9 denier fibers). An exemplary binder is a butadiene/styrene latex.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). The binder may be present in the acquisition layer 52 in excess of 12%, 14% or 16% by weight, but may be present by not more than 30%, or not more than 25% by weight of the acquisition layer. SB latex is available under the trade name GENFLO™ 3160 (OMNOVA Solutions Inc.; Akron, Ohio).

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13-15 gsm high wet strength made of cellulose fibers from supplier Havix.

The diaper may also comprise elasticized leg cuffs 32 and barrier leg cuffs 34, which provide improved containment of liquids and other body exudates especially in the area of the leg openings. Usually each leg cuffs 32 and barrier cuffs 34 will comprise one or more elastic string 33 and 35, represented in exaggerated form on FIGS. 1 and 2. Moreover, the diaper 20 may comprise other features such as back ears 40, front ears 46 and/or barrier cuffs 34 attached to form the composite diaper structure. The diaper may further comprise a fastening system, such as an adhesive fastening system or a mechanical fastening system (e.g. a hook and loop fastening system), which can comprise tape tabs 42, such as adhesive tape tabs or tape tabs comprising hook elements, cooperating with a landing zone 44 (e.g. a nonwoven web providing loops in a hook and loop fastening system). Further, the diaper may comprise other elements, such as a back elastic waist feature and a front elastic waist feature, side panels or a lotion application.

The diaper 20 as shown in FIGS. 1 and 2 can be notionally divided in a first waist region 36, a second waist region 38 opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper. The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20.

Feminine Care Absorbent Article

A feminine care absorbent article generally comprises at least a backsheet, a topsheet which is joined to the backsheet, and typically an absorbent structure disposed between the backsheet and the topsheet.

A pantiliner generally has two end regions and a middle region (i.e. a crotch region). The pantiliner has a body-facing surface and a garment facing surface.

The size and shape of the absorbent structure positioned between the topsheet and the backsheet can be altered to meet absorbent capacity requirements, and to provide comfort to the wearer. The absorbent structure suitable for use in the present invention can be any liquid-absorbent material known in the art for use in absorbent articles. The absorbent structure may comprise or consist of the polyacrylic acid crosslinked cellulosic fibers disclosed herein.

While the pantiliner may have any shape known in the art, a typical shape is generally "hourglass" shaped.

The garment facing surface of the pantiliner can have thereon pressure sensitive adhesive for affixing to a wearer's undergarments. Typically, such adhesive is covered with a release strip which is removed before affixing to the undergarment.

Pantiliners can also be provided with lateral extensions known commonly in the art as "flaps" or "wings" (not shown) intended to extend over and cover the panty elastics in the crotch region of the user's undergarment. However, wings are normally not used with pantiliners but are more often used in sanitary napkins.

Paper Product

A paper product generally comprises are consists of a fibrous structure. The fibrous structures can be single-ply or multi-ply fibrous structures and can comprise cellulosic pulp fibers. Especially, the fibrous structure can comprise or consist of the polyacrylic acid crosslinked cellulosic fibers disclosed herein. Other naturally-occurring and/or non-naturally occurring fibers can also be present in the fibrous structures. The fibrous structures can be throughdried, or "through air dried (TAD)". The fibrous structures can be wet-laid fibrous structures. The fibrous structures can be incorporated into single- or multi-ply paper products. The paper products can be in roll form where they are convolutedly wound or wrapped about themselves with or without the employment of a core. Alternatively, the paper products or fibrous structures can be in sheet form or can be at least partially folded over themselves.

EXAMPLES

The following examples describe illustrative, non-limiting embodiments and methods of subsequently treating polyacrylic acid crosslinked cellulosic fibers with hydrogen peroxide in amounts effective to reduce the amount of furfural (and accompanying malodor) in the crosslinked fibers.

Example 1

Samples of polyacrylic acid crosslinked cellulose fibers were prepared on lab scale by treating southern pine kraft pulp fibers (CF416, Weyerhaeuser Co.) with polyacrylic acid (Aquaset 1676, Dow). All samples were treated with a standard crosslinking solution and cured at 193° C. (380° F.) for 5 minutes. The cured fibers were remoisturized either with distilled water (as control) or with water containing the bleaching agent hydrogen peroxide ($H_2O_2$) at concentrations of 1.13 kg/ADMT (2.5 lbs/ADMT), 2.27 kg/ADMT (5.0 lbs/ADMT), 3.4 kg/ADMT (7.5 lbs/ADMT), and 4.54 kg/ADMT (10.0 lbs/ADMT) of fiber. The pH of distilled water was 4.46, and that of the respective $H_2O_2$ solutions were 4.96, 4.72, 4.80, and 4.65.

The following procedure using GC-FID equipment was used for measuring the amount of furfural generated in the polyacrylic acid crosslinked cellulosic fibers and its reduction after the application of bleaching agent, i.e. hydrogen peroxide.

One gram of the pulp sample was inserted into a 20 ml vial, capped and heated for 10 minutes at 85° C. in a Headspace Sampler (HP 7694). Volatile compounds are driven off of the pulp into the headspace in the form of vapors. The Headspace Sampler injects the gas sample, via a 0.5 ml sample loop, onto a HP 5890 Series II Gas Chromatograph (GC). A 30 meter megabore column (DB624 0.054 mm ID, 3.0 micron film thickness) separates the compounds by a combination of boiling point, molecular weight and vapor pressure—as the GC oven heats up, the compounds elute off of the column and are detected by a flame ionization detector (FID). The resulting graph is represented by distinct peaks over the time of the analysis. The data is acquired by HP Chemstation software and analyzed by Thermo Target Software. The compound is identified by its unique retention time and the intensity (the peak area) indicates the amount. For furfural, nine different concentrations were used to generate a calibration curve, with a range from 0.02-12 µg/g (ppm). The calibration curve had a regression of R squared of 0.999.

Post-treatment furfural levels of the samples are shown in Table 1, below. "Day 0" indicates day of production and subsequent bleaching treatment.

TABLE 1

| Sample | Bleach treatment (kg/ADMT) | | Amount of furfural (µg/g (ppm)) | | | |
|---|---|---|---|---|---|---|
| | $H_2O_2$ | NaOH | Day 0 | Day 1 | Day 5 | Day 12 |
| 1A | 0.0 | 0.0 | 2.9 | — | — | — |
| 1B | 1.13 | 0.0 | 2.7 | 2.5 | 2.3 | 1.3 |
| 1C | 2.27 | 0.0 | 2.5 | 2.3 | 2.1 | 1.2 |
| 1D | 3.40 | 0.0 | 2.4 | 2.4 | 2.2 | 1.9 |
| 1E | 4.54 | 0.0 | 2.2 | 2.1 | 1.9 | 1.7 |

Furfural content of the treated samples (1B, 1C, 1D, and 1E) at Day 1, compared to that of the untreated control sample (1A), generally decreased as the amount of hydrogen peroxide applied increased, with reductions of approximately 14%, 21%, 17%, and 28% observed at the 1.13 kg/ADMT (2.5 lbs/ADMT), 2.27 kg/ADMT (5.0 lbs/ADMT), 3.4 kg/ADMT (7.5 lbs/ADMT), and 4.54 kg/ADMT (10.0 lbs/ADMT) of fiber levels, respectively.

With aging, the greatest amount of furfural reduction was observed in samples 1B and 1C, at the 1.13 kg/ADMT (2.5 lbs/ADMT) and 2.27 kg/ADMT (5.0 lbs/ADMT) of fiber levels, respectively. At each of these two levels, furfural content was reduced by approximately 48% between Day 1 and Day 12.

Overall, the furfural reduction compared to the untreated control sample (1A) was greatest in samples 1B and 1C, at the 1.13 kg/ADMT (2.5 lbs/ADMT) and 2.27 kg/ADMT (5.0 lbs/ADMT) of fiber levels, respectively, at Day 12. At these levels, furfural content was reduced in sample 1B by approximately 55% compared to the untreated control sample, and in sample 1C by approximately 59% compared to the untreated control sample.

Example 2

Samples of polyacrylic acid crosslinked cellulose fibers were prepared on lab scale according to the procedure described in Example 1. However, after treatment with crosslinking solution, samples were cured at 193° C. (380° F.) for 10 minutes in order to enhance initial levels of furfural resulting from curing. The cured fibers were remoisturized either with water (control), or with water containing the bleaching agent hydrogen peroxide ($H_2O_2$) at concentrations of 1.13 kg/ADMT (2.5 lbs/ADMT), 2.27 kg/ADMT (5.0 lbs/ADMT), 3.4 kg/ADMT (7.5 lbs/ADMT), and 4.54 kg/ADMT (10.0 lbs/ADMT) of fiber. Some cured fibers were treated with water containing $H_2O_2$ (at concentrations of 1.13 kg/ADMT (2.5 lbs/ADMT) and 2.27 kg/ADMT (5.0 lbs/ADMT) fiber) and sodium hydroxide (NaOH) (at a concentration of either 1.13 kg/ADMT (2.5 lbs/ADMT) or 2.27 kg/ADMT (5.0 lbs/ADMT) fiber).

Post-treatment furfural levels of the samples, determined by the GC-FID procedure described in Example 1, are shown in Table 2, below.

TABLE 2

| Sample | Bleach treatment (kg/ADMT) | | Amount of furfural (µg/g (ppm)) | | | |
|---|---|---|---|---|---|---|
| | $H_2O_2$ | NaOH | Day 0 | Day 1 | Day 7 | Day 14 |
| 2A | 0.0 | 0.0 | 6.5 | — | — | — |
| 2B | 1.13 | 0.0 | 4.4 | 4.4 | 3.5 | 3.1 |
| 2C | 1.13 | 1.13 | 4.4 | 4.2 | 3.4 | 2.9 |
| 2D | 2.27 | 0.0 | 4.7 | 4.2 | 3.7 | 3.1 |
| 2E | 2.27 | 1.13 | 4.8 | 4.3 | 3.4 | 3.6 |
| 2F | 2.27 | 2.27 | 3.9 | 3.9 | 3.5 | 3.2 |
| 2G | 3.4 | 0.0 | 4.2 | 3.5 | 3.1 | 2.9 |
| 2H | 4.54 | 0.0 | 2.8 | 3.2 | 3.3 | 2.5 |

Again, furfural content of the treated samples generally decreased as the amount of hydrogen peroxide applied increased, comparing Day 1 values to that of the untreated control sample (2A), with reductions ranging from approximately 32% (in sample 2B) to approximately 51% (in sample 2H). Furfural content at Day 1 was slightly less in the samples treated with sodium hydroxide in addition to hydrogen peroxide, as compared with the samples treated with the same amount of hydrogen peroxide alone.

With aging, as with Example 1, the greatest amount of furfural reduction was observed at the 1.13 kg/ADMT (2.5 lbs/ADMT) and 2.27 kg/ADMT (5.0 lbs/ADMT) of fiber levels. At the lower of these levels, the extent of furfural reduction from Day 1 to Day 14 was slightly greater in the presence of sodium hydroxide: approximately 30% in sample 2B (treated with $H_2O_2$ alone) vs. approximately 31% in sample 2C (treated with $H_2O_2$ in the presence of NaOH). However, at the higher of these levels, the extent of furfural reduction after Day 1 was lower in the presence of sodium hydroxide: approximately 26% in sample 2D (treated with $H_2O_2$ alone) vs. approximately 21% and 18% in samples 2E and 2F, respectively (treated with $H_2O_2$ in the presence of 1.13 kg NaOH per ADMT (2.5 lbs/ADMT) and 2.27 kg NaOH/ADMT (5.0 lbs NaOH per ADMT) of fiber, respectively).

Overall, in Example 2, the furfural reduction compared to the untreated control sample (2A) was greatest in sample 2H (at 4.54 kg/ADMT (10.0 lbs/ADMT) of fiber) at Day 14, at approximately 62%.

Example 3

A mill trial was conducted to apply varying levels of hydrogen peroxide to polyacrylic acid crosslinked cellulose fibers produced at the Weyerhaeuser Company's Columbus Modified Fiber mill in Columbus, Miss. The polyacrylic acid crosslinked fibers were produced from southern kraft pulp fibers (CF416, Weyerhaeuser Co.). Water, containing the bleaching agent hydrogen peroxide ($H_2O_2$) at concentrations of 1.13 kg/ADMT (2.5 lbs/ADMT), 1.56 kg/ADMT (3.5 lbs/ADMT), and 2.27 kg/ADMT (5.0 lbs/ADMT) of fiber, was used to remoisturize cured fibers, by spraying the solution into an air stream containing the cured fibers.

The polyacrylic acid crosslinked cellulosic fibers were cured in a curing bin at temperature of about 182° C. for about 4.5-5 minutes.

Post-treatment furfural levels of the samples, determined by the GC-FID procedure described in Example 1, are shown in Table 3, below.

TABLE 3

| Sample | Bleach treatment (kg/ADMT) | | Amount of furfural (µg/g (ppm)) | | |
|---|---|---|---|---|---|
| | $H_2O_2$ | NaOH | Day 1 | Day 7 | Day 21 |
| 3A | 0.0 | 0.0 | 1.8 | — | — |
| 3B | 1.13 | 0.0 | 1.507 | 1.307 | 1.163 |
| 3C | 1.59 | 0.0 | 1.093 | 0.917 | 0.748 |
| 3D | 2.27 | 0.0 | 0.760 | 0.570 | 0.393 |

Consistent with Examples 1 and 2, the furfural content of the treated samples decreased as the amount of hydrogen peroxide applied in the mill trial increased, comparing Day 1 values to that of the untreated control sample (3A), with reductions ranging from approximately 16.3% to approximately 57.8%.

With aging, the greatest amount of furfural reduction after Day 1 was observed at the 5.0 lbs/ADMT of fiber level, at approximately 48.3%. Furfural reduction at the lower levels was approximately 31.6% at the 1.59 kg/ADMT (3.5 lbs/ADMT) of fiber level, and approximately 22.8% at the 1.13 kg/ADMT (2.5 lbs/ADMT) of fiber level.

Overall, in the mill trial, the furfural reduction at Day 21 compared to the untreated control sample (3A) was approximately 35.4% in sample 3B (at 1.13 kg/ADMT (2.5 lbs/ADMT) of fiber), approximately 58.4% in sample 3C (at 1.59 kg/ADMT (3.5 lbs/ADMT) of fiber), and approximately 78.2% in sample 3D (at 2.27 kg/ADMT (5.0 lbs/ADMT) of fiber).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising polyacrylic acid crosslinked cellulosic fibers, wherein the polyacrylic acid crosslinked cellulosic fibers are treated with hydrogen peroxide in an amount of from about 0.045 kg to about 9.07 kg per ADMT of fiber in the absence of sodium hydroxide, wherein the amount of furfural in the treated polyacrylic acid crosslinked cellulosic fibers is reduced from a first value determined at least one day after treatment of the polyacrylic acid crosslinked cellulosic fibers to a second, subsequent value determined up to 21 days after treatment, wherein the polyacrylic acid crosslinked cellulosic fibers are treated with hydrogen peroxide prior to being incorporated into the absorbent article.

2. The absorbent article of claim 1, wherein the polyacrylic acid crosslinked cellulosic fibers have less than about 0.4 ppm furfural up to 21 days after the treatment.

3. The absorbent article of claim 1, wherein the reduction of furfural from the first value to the second value is at least about 25%.

4. The absorbent article of claim 1, wherein the treatment of the polyacrylic acid crosslinked cellulosic fibers is in the absence of alkaline agents.

5. The absorbent article of claim 1, wherein the treatment of the polyacrylic acid crosslinked cellulosic fibers is with hydrogen peroxide alone.

6. An absorbent article comprising polyacrylic acid crosslinked cellulosic fibers, wherein the polyacrylic acid crosslinked cellulosic fibers have less than about 1.3 ppm furfural.

7. The absorbent article of claim 6, wherein the polyacrylic acid crosslinked cellulosic fibers are treated subsequent to curing with hydrogen peroxide in the absence of alkaline agents, wherein the polyacrylic acid crosslinked cellulosic fibers are treated with hydrogen peroxide prior to being incorporated into the absorbent article.

8. The absorbent article of claim 6, wherein the treatment of the polyacrylic acid crosslinked cellulosic fibers is with hydrogen peroxide alone and wherein the polyacrylic acid crosslinked cellulosic fibers are treated with hydrogen peroxide prior to being incorporated into the absorbent article.

9. An absorbent article comprising polyacrylic acid crosslinked cellulosic fibers, wherein the polyacrylic acid crosslinked cellulosic fibers are treated with hydrogen peroxide in an amount of from about 0.045 kg to about 9.07 kg per ADMT of fiber in the absence of alkaline agents, wherein the amount of furfural in the treated polyacrylic acid crosslinked cellulosic fibers is reduced by at least about 55%, as measured up to 21 days after the treatment, versus the untreated fibers, wherein the polyacrylic acid crosslinked cellulosic fibers are treated with hydrogen peroxide prior to being incorporated into the absorbent article.

10. The absorbent article of claim 1, wherein the absorbent article is selected from the group consisting of a diaper, a pant, an absorbent insert for a diaper or pant, a sanitary napkin, a pantiliner, a wet wipe, a dry wipe, and a paper product, such as toilet tissue and paper towel.

11. The absorbent article of claim 6, wherein the absorbent article is selected from the group consisting of a diaper, a pant, a sanitary napkin, and a pantiliner, and wherein the absorbent article comprises a topsheet, a backsheet, an absorbent core disposed between the topsheet and backsheet.

12. The absorbent article of claim 9, wherein the absorbent article is selected from the group consisting of a diaper, a pant, a sanitary napkin, and a pantiliner, and wherein the absorbent article comprises a topsheet, a backsheet, an absorbent core disposed between the topsheet and backsheet, and an acquisition-distribution system disposed between the topsheet and the absorbent core, wherein the polyacrylic acid crosslinked cellulosic fibers form all of or form a layer of the acquisition-distribution system.

13. A method of making an absorbent article, the absorbent article comprising polyacrylic acid crosslinked cellulosic fibers, the method comprising the reduction of the furfural content of the polyacrylic acid crosslinked cellulosic fibers prior to introducing the polyacrylic acid crosslinked cellulosic fibers into the absorbent article, wherein reducing the furfural content of the polyacrylic acid crosslinked cellulosic fibers comprises applying hydrogen peroxide alone, in a bleaching stage subsequent to a curing stage, to the polyacrylic acid crosslinked cellulosic fibers in an amount of from about 0.045 kg to about 9.07 kg per ADMT of fiber and at a pH of between about 4.5 and 5, wherein the amount of furfural in the treated polyacrylic acid crosslinked cellulosic fibers reduces from a first value determined at least one day after the treatment of the polyacrylic acid crosslinked cellulosic fibers to a second, subsequent value determine up to 21 days after treatment.

14. The method of claim 13, wherein the hydrogen peroxide is applied by spraying the hydrogen peroxide alone into an air stream containing the polyacrylic acid crosslinked cellulosic fibers.

15. The method of claim 13, wherein the reduction of furfural from the first value to the second value is at least about 25%.

16. The method of claim 13, wherein the reduction of furfural for the second value is at least about 55% as compared to the untreated polyacrylic acid crosslinked cellulosic fibers.

17. A method of reducing the malodor associated with the presence of furfural in polyacrylic acid crosslinked cellulosic fibers comprising applying hydrogen peroxide in the absence of alkaline agents to the polyacrylic acid crosslinked cellulosic fibers subsequent to curing the polyacrylic acid crosslinked cellulosic fibers, and thereby reducing the furfural content of the polyacrylic acid crosslinked cellulosic fibers by at least about 55% versus the untreated fibers, and wherein the treated polyacrylic acid crosslinked cellulosic fibers are subsequently incorporated into an absorbent article.

18. The method of claim 17, further comprising allowing the polyacrylic acid crosslinked cellulosic fibers to age up to 21 days following the application of hydrogen peroxide and prior to determining the reduction of furfural content.

19. The method of claim 17, wherein the hydrogen peroxide is applied to the polyacrylic acid crosslinked cellulosic fibers at a pH of between about 4.5 and 5.

20. The method of claim 13, wherein the absorbent article is selected from the group consisting of a diaper, a pant, an absorbent insert for a diaper or pant, a sanitary napkin, a pantiliner, a wet wipe, a dry wipe, and a paper products, such as toilet tissue and paper towel.

* * * * *